（12） United States Patent
Wegelin et al.

(10) Patent No.: US 10,977,886 B2
(45) Date of Patent: Apr. 13, 2021

(54) MODULAR PEOPLE COUNTERS

(71) Applicant: GOJO Industries, Inc., Akron, OH (US)

(72) Inventors: Jackson W. Wegelin, Stow, OH (US); Chip W. Curtis, West Dundee, IL (US); Dennis K. Jenkins, Akron, OH (US); Mark A. Bullock, Wooster, OH (US)

(73) Assignee: GOJO Industries, Inc., Akron, OH (US)

( * ) Notice: Subject to any disclaimer, the term of this patent is extended or adjusted under 35 U.S.C. 154(b) by 0 days.

(21) Appl. No.: 16/274,597

(22) Filed: Feb. 13, 2019

(65) Prior Publication Data
US 2019/0251766 A1     Aug. 15, 2019

Related U.S. Application Data

(60) Provisional application No. 62/629,777, filed on Feb. 13, 2018.

(51) Int. Cl.
*G05G 19/00*     (2006.01)
*G07C 9/28*      (2020.01)
(Continued)

(52) U.S. Cl.
CPC .............. *G07C 9/28* (2020.01); *G07C 11/00* (2013.01); *G08B 21/245* (2013.01); *G16H 40/20* (2018.01);
(Continued)

(58) Field of Classification Search
CPC ....... G07C 9/00111; G07C 11/00; G07C 7/00; G16H 40/20; G08B 21/245; G06K 9/00369; G06M 1/02
(Continued)

(56) References Cited

U.S. PATENT DOCUMENTS

| 4,278,878 A   | 7/1981 | Kato |             |
|---------------|--------|------|-------------|
| 7,782,214 B1* | 8/2010 | Lynn | G09B 19/0076 |
|               |        |      | 340/573.1   |

(Continued)

FOREIGN PATENT DOCUMENTS

EP     1593102 A1     11/2005

OTHER PUBLICATIONS

International Search Report from PCT/US2019/017807 dated May 20, 2019 (15 pages).

*Primary Examiner* — Zhen Y Wu
(74) *Attorney, Agent, or Firm* — Calfee, Halter & Griswold LLP

(57) ABSTRACT

An exemplary embodiment of a modular people counter includes a base and a communications module. The base has a people counter processor, memory, a power supply having one or more batteries, a passive sensor that detects whether a badge and/or a person has entered into a selected area and is within the sensing range and a first connector. The first connector is in circuit communication with the people counter processor. The communications module has a second connector for connecting to the first connector and wireless communications circuitry. The wireless communications module is configured to receive one or more signals from the people counter processor when the first connector is connected to the second connector.

18 Claims, 6 Drawing Sheets

(51) Int. Cl.
*G16H 40/20* (2018.01)
*G07C 11/00* (2006.01)
*G08B 21/24* (2006.01)
*G06M 1/02* (2006.01)
*G07C 7/00* (2006.01)
*G06K 9/00* (2006.01)

(52) U.S. Cl.
CPC ............ *G06K 9/00369* (2013.01); *G06M 1/02* (2013.01); *G07C 7/00* (2013.01)

(58) Field of Classification Search
USPC ........................................................ 340/5.61
See application file for complete search history.

(56) References Cited

U.S. PATENT DOCUMENTS

| | | | | |
|---|---|---|---|---|
| 8,123,694 B2* | 2/2012 | Kinsley | ............... | A61B 5/02141 600/492 |
| 8,248,204 B2* | 8/2012 | Takeshima | ......... | G06K 7/10128 340/4.34 |
| 9,041,531 B1* | 5/2015 | DeLand | ................. | A61B 6/107 340/539.12 |
| 10,026,278 B1* | 7/2018 | Asaro | .................... | G08B 7/062 |
| 10,607,471 B2* | 3/2020 | Hood | .................... | G16H 40/20 |
| 2003/0169337 A1* | 9/2003 | Wilson | ................... | H04N 7/181 348/156 |
| 2004/0239777 A1* | 12/2004 | Nakamura | ......... | H04N 1/00161 348/239 |
| 2005/0093986 A1* | 5/2005 | Shinohara | .......... | H04N 1/00167 348/208.1 |
| 2005/0154919 A1* | 7/2005 | Noguchi | ............. | G06F 21/6254 726/4 |
| 2008/0062283 A1* | 3/2008 | Matsushita | ............ | H04N 5/232 348/231.99 |
| 2008/0219659 A1* | 9/2008 | Tian | .................... | H01M 2/1022 396/539 |
| 2009/0087028 A1* | 4/2009 | Lacey | .................. | G08B 21/245 382/103 |
| 2009/0179742 A1* | 7/2009 | Takeshima | ........... | G06K 7/0008 340/10.1 |
| 2009/0265215 A1* | 10/2009 | Lindstrom | ......... | G06Q 30/0203 705/7.32 |
| 2009/0315678 A1* | 12/2009 | Padmanabhan | .......... | H04Q 9/00 340/10.1 |
| 2010/0061703 A1* | 3/2010 | Pham | ...................... | G01P 15/18 386/241 |
| 2010/0308076 A1* | 12/2010 | Snodgrass | ............ | B65D 83/262 222/52 |
| 2010/0315244 A1* | 12/2010 | Tokhtuev | ................. | G06Q 10/00 340/603 |
| 2011/0163870 A1* | 7/2011 | Snodgrass | ........... | A61B 5/1122 340/539.11 |
| 2011/0291841 A1* | 12/2011 | Hollock | ............... | G08B 21/245 340/573.1 |
| 2012/0212344 A1* | 8/2012 | Forsberg | .............. | G08B 21/245 340/573.1 |
| 2012/0218106 A1* | 8/2012 | Zaima | .................... | H04W 4/027 340/540 |
| 2013/0015355 A1 | 1/2013 | Noone et al. | | |
| 2013/0027199 A1* | 1/2013 | Bonner | ................ | G08B 21/245 340/539.11 |
| 2013/0229276 A1* | 9/2013 | Hunter | .................. | G08B 21/245 340/501 |
| 2014/0253336 A1* | 9/2014 | Ophardt | ................. | G08C 17/02 340/573.1 |
| 2014/0361909 A1* | 12/2014 | Stelfox | ................. | G06F 16/955 340/870.07 |
| 2015/0183618 A1* | 7/2015 | Kondo | .................... | B66B 1/468 187/380 |
| 2015/0194043 A1* | 7/2015 | Dunn | .................... | G08B 21/245 340/573.1 |
| 2015/0287296 A1* | 10/2015 | Hall | ....................... | G01S 5/0294 340/541 |
| 2015/0355308 A1* | 12/2015 | Ishida | ...................... | G01S 5/12 455/456.1 |
| 2015/0379494 A1* | 12/2015 | Hiroi | ................... | H04N 5/23293 705/16 |
| 2016/0180688 A1* | 6/2016 | O'Toole | ................ | G06Q 10/06 340/517 |
| 2016/0203699 A1* | 7/2016 | Mulhern | ................... | G08B 5/22 340/573.1 |
| 2016/0227348 A1* | 8/2016 | Guo | ...................... | H04L 9/3278 |
| 2016/0358440 A1* | 12/2016 | Trivelpiece | ............. | G01S 11/04 |
| 2016/0371619 A1* | 12/2016 | Foster | ................ | G06Q 10/0637 |
| 2017/0098366 A1* | 4/2017 | Hood | ..................... | G16H 40/20 |
| 2017/0134887 A1* | 5/2017 | Wegelin | ................. | H04W 4/80 |
| 2018/0068025 A1* | 3/2018 | Gadepalli | ............. | G06F 16/248 |
| 2018/0301014 A1* | 10/2018 | Worral | ................ | G06K 9/00355 |
| 2019/0081426 A1* | 3/2019 | Chavakula | ............. | H01R 27/00 |
| 2019/0122015 A1* | 4/2019 | Huang | ............... | G06K 7/10475 |
| 2019/0243551 A1* | 8/2019 | Xu | ........................ | G06F 3/0605 |
| 2019/0282095 A1* | 9/2019 | Bedingham | .......... | A61B 5/6823 |
| 2020/0106205 A1* | 4/2020 | Carr, Jr. | ................ | H01R 4/5008 |

* cited by examiner

MODULAR PEOPLE COUNTERS

RELATED APPLICATIONS

This application claims priority to and the benefits of U.S. Provisional Pat. App. No. 62/629,777 titled Modular People Counter, filed on Feb. 13, 2018, and which is incorporated herein by reference in its entirety.

TECHNICAL FIELD

The present invention generally relates to people counters, asset tracking and compliance monitoring systems. Particularly, the present invention relates to modular people counters for compliance monitoring systems and asset tracking.

BACKGROUND OF THE INVENTION

Compliance monitoring systems are designed to provide companies or institutions with knowledge relating to employees or workers compliance with selected hand-hygiene policies. Such companies and institutions include, for example, hospitals, food service industries, clinics, and the like. Several situations occur in which it is desirable to know whether a person, or a number of people (or other moving objects) are passing through or occupying an area, the time a person passes through an area, or other types of information for monitoring the movement of one or more people through an area. For example, a hospital administrator, for hygiene compliance purposes, may want to know the number of people that entered and/or exited a room having a hand soap/sanitizer dispenser, such that a comparison can be made between the number of people that entered and/or exited the room (i.e., number of opportunities for use of the dispenser) and the number of actual uses of the hand soap/sanitizer dispenser.

The monitoring of hand washing by individuals who are identified by electronic badges or data tags and then associating the badges or tags and individuals with the use of dispensers is known in the art. In addition, there are some automated system providers for hygiene compliance monitoring systems that use people counters with wireless communication circuitry for transmitting the location of persons. The dispensers, badges, and/or people counters transmits dispense events, user identification, and sometimes location to a central computer to record and analyze the usage data. Each of these systems utilize different types of communications protocols, transmitters, and the like.

Accordingly, for a people counter manufacturer to work with all of the providers, the people counter manufacturer must stock multiple circuit boards, some equipped for provider A's equipment, some equipped for provider B's equipment, some equipped for provider C's equipment, etc. Having multiple skews and products increases manufacturing complexity, increases required inventory, and the like, all of which drives up costs.

SUMMARY

Exemplary embodiments of modular people counters for compliance monitoring and asset tracking systems are disclosed herein. An exemplary embodiment of a modular people counter includes a base and a communications module. The base has a people counter processor, memory, a power supply having one or more batteries, a passive sensor that detects whether a badge and/or a person has entered into a selected area and is within the sensing range and a first connector. The first connector is in circuit communication with the people counter processor. The communications module has a second connector for connecting to the first connector and wireless communications circuitry. The wireless communications module is configured to receive one or more signals from the people counter processor when the first connector is connected to the second connector.

Another exemplary modular people counter includes a base and a wireless communications module. The base has a people counter processor, memory, a power source, a people sensor that detects whether one or more people have entered into a monitored area and are within its sensing range, and a first connector. The first connector is in circuit communication with the people counter processor. The communications module has a second connector for connecting to the first connector, a badge sensor that senses whether one or more badges are within its sensing range, and wireless communications circuitry. The wireless communications module is configured to receive one or more signals from the people counter processor.

Another exemplary modular people counter includes a base and a wireless communications module. The base has a housing, a people counter processor, memory, a power source, an active sensor that detects when a badge and/or person enters a monitored area and when the badge and/or person exits a monitored area, and a first connector. The first connector is in circuit communication with the people counter processor. The communications module has a housing, wireless communications circuitry and a second connector for connecting to the first connector to place the wireless communications circuitry in circuit communications with the people counter processor. The communications module is configured to receive one or more signals from the people counter processor when the first connector is connected to the second connector.

Another exemplary modular people counter for a compliance monitoring system includes a base and a communications module. The base has a people counter processor, memory, a power source, an active sensor that detects whether a badge and/or person is within the sensing range and a first connector. The connector in circuit communication with the power source and the people counter processor. The communications module has a second connector for connecting to the first connector and wireless communications circuitry. The communications module receives power from the base power source through the connector and is configured to receive one or more signals from the people counter processor when the first connector is connected to the second connector.

Another exemplary modular people counter includes a base and a wireless communications module. The base has a people counter processor, memory, a power supply having one or more batteries, and a passive sensor that detects whether a badge is within the sensing range; and a first connector. The connector is in circuit communication with the power source and the people counter processor. The communications module has a second connector for connecting to the first connector and wireless communications circuitry. The communications module receives power from the base power source through the connector and is configured to receive one or more signals from the people counter processor when the first connector is connected to the second connector.

Another modular people counter for a compliance system includes a base and a wireless communications module. The base has a people counter processor, memory, a power supply having one or more batteries and a sensor that detects whether a badge is within the sensing range, and a first connector. The first connector is in circuit communication with the power source and the people counter processor. The wireless communications module has a second connector for connecting to the first connector; wireless communications circuitry and a communications module processor. The communications module receives power from the base power source through the connector and is configured to receive one or more signals from the people counter processor when the first connector is connected to the second connector.

Yet another exemplary modular people counter includes a base and a communications module. The base has a people counter processor, memory, a power source, a people sensor that detects whether one or more people are within its sensing range, and a first connector. The first connector is in circuit communication with the power source and the people counter processor. The communications module has a second connector for connecting to the first connector, a badge sensor that senses whether one or more badges are within its sensing range; and wireless communications circuitry. The communications module receives power from the base power source through the connector and is configured to receive one or more signals from the people counter processor when the first connector is connected to the second connector.

BRIEF DESCRIPTION OF THE DRAWINGS

These and other features and advantages of the present invention will become better understood with regard to the following description and accompanying drawings in which.

DETAILED DESCRIPTION

Figure 1:
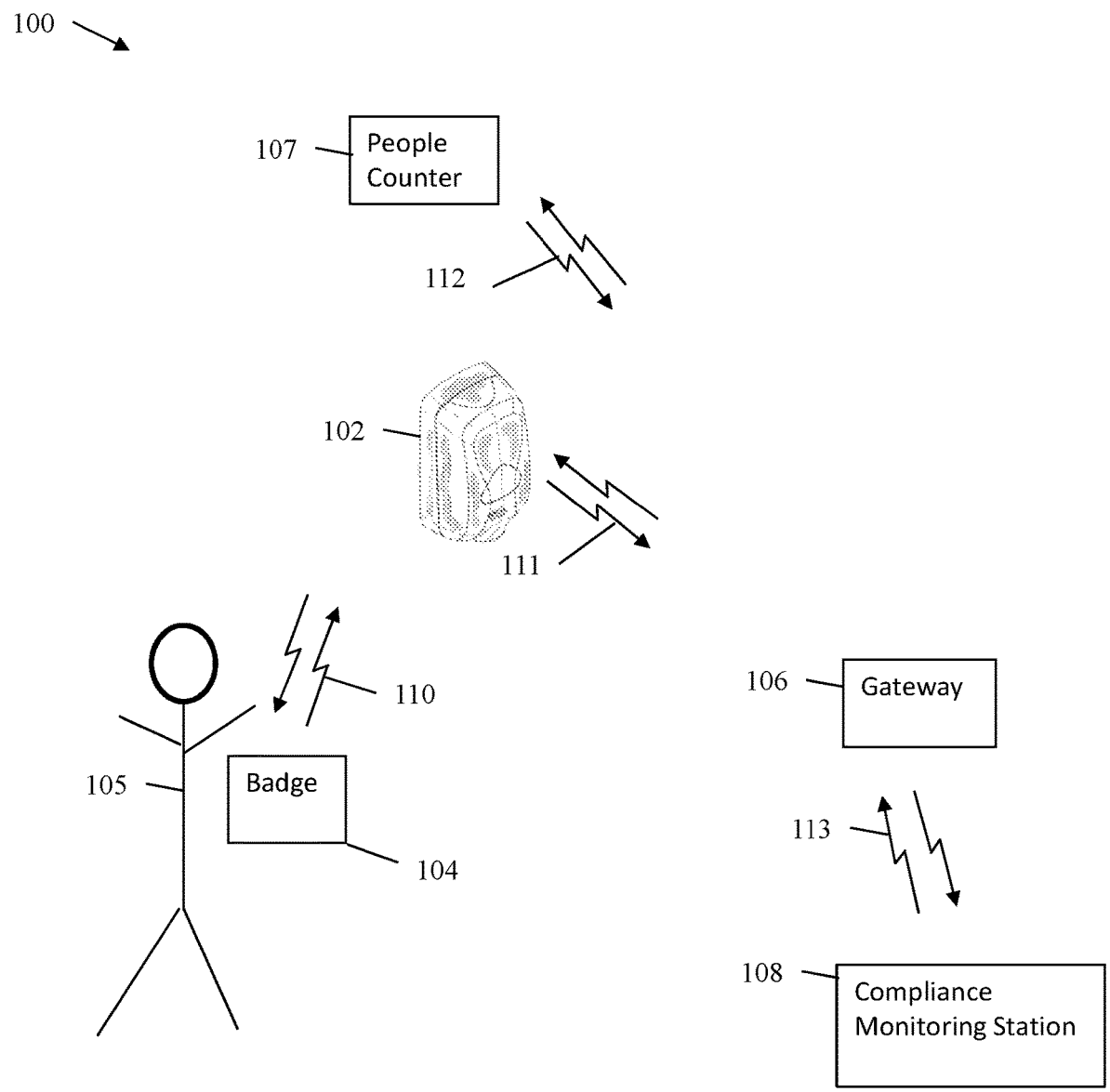
FIG. 1 is illustrative of an exemplary compliance monitoring system having a modular people counter.

The following includes definitions of exemplary terms used throughout the disclosure. Both singular and plural forms of all terms fall within each meaning. Except where noted otherwise, capitalized and non-capitalized forms of all terms fall within each meaning:

"Circuit communication" as used herein indicates a communicative relationship between devices. Direct electrical, electromagnetic and optical connections and indirect electrical, electromagnetic and optical connections are examples of circuit communication. Two devices are in circuit communication if a signal from one is received by the other, regardless of whether the signal is modified by some other device. For example, two devices separated by one or more of the following—amplifiers, filters, transformers, optoisolators, digital or analog buffers, analog integrators, other electronic circuitry, fiber optic transceivers or satellites—are in circuit communication if a signal from one is communicated to the other, even though the signal is modified by the intermediate device(s). As another example, an electromagnetic sensor is in circuit communication with a signal if it receives electromagnetic radiation from the signal. As a final example, two devices not directly connected to each other, but both capable of interfacing with a third device, such as, for example, a CPU, are in circuit communication. Circuit communication includes providing power to one or more devices. For example, a processor may be in circuit communication with one or more batteries, indicating that the batteries provide power to the processor.

Also, as used herein, voltages and values representing digitized voltages are considered to be equivalent for the purposes of this application, and thus the term "voltage" as used herein refers to either a signal, or a value in a processor representing a signal, or a value in a processor determined from a value representing a signal.

"Signal", as used herein includes, but is not limited to one or more electrical signals, power signals, analog or digital signals, one or more computer instructions, a bit or bit stream, or the like.

"Logic," synonymous with "circuit" as used herein includes, but is not limited to hardware, firmware, software and/or combinations of each to perform a function(s) or an action(s). For example, people counter based on a desired application or needs, logic may include a software controlled microprocessor or microcontroller, discrete logic, such as an application specific integrated circuit (ASIC) or other programmed logic device. Logic may also be fully embodied as software. The circuits identified and described herein may have many different configurations to perform the desired functions.

Any values identified in the detailed description are exemplary and they are determined as needed for a particular dispenser and/or refill design. Accordingly, the inventive concepts disclosed and claimed herein are not limited to the particular values or ranges of values used to describe the embodiments disclosed herein.

Power connection as used herein indicates a power relationship between devices. Direct electrical connections as well as inductive power connections are examples of circuit communication.

The term people counter as used herein does not require the system to count people. In many cases, the people counter is used to locate a badge or tag. Typically, the badge or tag is associated with, and/or secured to a person, however, in some embodiments, the badge or tag is associated with an asset. Accordingly, the people counter may detect an asset that is associated with the badge or tag, a badge or tag attached to a person, or simply a person.

In addition, the term "badge" or "tag" as used herein may be a stand-alone device, or may be an integrated device, such as, for example, a smart phone, tablet, iPad, or the like. In some embodiments, the integrated device may include application software so that the device performs any of the required functions described herein.

In some embodiments, the people counter may detect a signal, such as, for example, a BlueTooth signal emitted form that badge, smart phone, tablet, iPad or other device. In some embodiments, the people counter may cause the badge or other device to emit a signal detectable by the people counter.

FIG. 1 illustrates an exemplary embodiment of compliance monitoring system 100. Compliance monitoring system 100 includes a plurality of dispensers 102 (only 1 is shown for clarity), a plurality of badges 104 (only 1 is shown for clarity), one or more gateways 106 (in some instances gateways 106 are not required) a plurality of peoples counter 107 (only 1 is shown for clarity), and a compliance monitoring station 108. Compliance monitoring station 108 may be, for example, a computer having software for determining, inter alia, one or more compliance rates for individuals based on the number of dispenses of soap or sanitizer delivered to an individual divided by the number of opportunities that the person should have washed or sanitized their hands.

Dispenser 102 may be any type of dispenser, such as, for example, a touch free dispenser. Exemplary touch-fee dispensers are shown and described in U.S. Pat. No. 7,837,066 titled Electronically Keyed Dispensing System And Related Methods Utilizing Near Field Response; U.S. Pat. No. 9,172,266 title Power Systems For Touch Free Dispensers and Refill Units Containing a Power Source; U.S. Pat. No. 7,909,209 titled Apparatus for Hands-Free Dispensing of a Measured Quantity of Material; U.S. Pat. No. 7,611,030 titled Apparatus for Hans-Free Dispensing of a Measured Quantity of Material; U.S. Pat. No. 7,621,426 titled Electronically Keyed Dispensing Systems and Related Methods Utilizing Near Field Response; and U.S. Pat. No. 8,960,498 titled Touch-Free Dispenser with Single Cell Operation and Battery Banking; all which are incorporated herein by reference. In some embodiments, the dispenser may be a manually operated dispenser. In such a dispenser, a user manually causes the dispenser to dispense product. The user may manually cause the dispenser to dispense product by, for example, pressing a push-bar; pulling a lever; pushing a lever; stepping on a foot activated pump; and the like.

In some embodiments, dispenser 102 is equipped with wireless communication circuitry. In some embodiments, the wireless circuitry includes longer range communication, such as, for example, an RF transceiver; in some embodiments, the wireless circuitry includes near field communications such as, for example, BlueTooth® transmitter/receiver. Other types of wireless circuitry, such as, for example, BLE, Infrared ("IR") or ANT®, may also be used. Dispenser 102 may communicate with a badge 104 carried by a person 105, and/or with gateway 106.

Badge 104 is often proprietary to compliance system provider. In some embodiments, badge 104 transmits to and/or receives signals 110 from people counter 107 and dispenser 102. In some embodiments, badge 104 transmits a signal 110, but does receive signals. In some embodiments, badge 104 repeatedly transmits signal 110. In some embodiments, badge 104 transmits signals 110 to people counter 107 and dispenser 102 using near field communications, such, as BLE, Ant, BlueTooth, IR and the like. In some embodiments, badge 104 transmits signals 110 directly to the gateway 106 or compliance monitoring station 108 using an RF transmitter, or a WIFI transmitter. In some embodiments, badge 104 transmits and receives signals from people counter 107 and/or dispenser 102. In some embodiments, badge 104 utilizes a first communications protocol. In some embodiments, badge 104 utilizes a second communications protocol. In some embodiments, badge 104 utilizes a third communications protocol.

As the badges 104 are typically proprietary to the compliance system provider, not all badges utilize the same hardware, software and/or communications protocols. Accordingly, manufacture A may have hardware A, software A and/or communications protocols A. Manufacture B may have hardware B, software B and/or communications protocols B. Accordingly, manufacture C may have hardware C, software C and/or communications protocols C. Although Hardware A, B, C, software A, B, C and/or communications protocols A, B, C may have similar or the same components, they generally have differences that prevent them from being used interchangeably.

People counters 107 are typically mounted above selected areas and are typically mounted to the ceiling. In some embodiments, people counters 107 are located proximate entries/exits to areas. In some embodiments, a first people counter 107 is located in a hallway outside of a room and a second people counter 107 is located in the room. In some embodiments, a people counter 107 is located in a center of a room. In some embodiments, multiple people counters 107 are located in each room. In some embodiments, two or more people counters 107 are used to determine the direction of travel of a person or asset. In some embodiments, people counters utilize strength of signal to determine the direction of travel of a person or asset.

In some embodiments, people counter 107 is a passive device. If people counter 107 is a passive device, people counter 107 may listen for a signal from a badge 104 indicating that person (or asset) 105 has entered into the room or area being monitored by people counter 107. Exemplary passive detectors may include, for example, passive IR detector, a passive RFID detector, or any other type detector that listens for a transmission without the need to initiate the transmission.

In some embodiments, people counter 107 is an active device. If the people counter 107 is an active device, people counter 107 has an active sensor to detect the presence of a person. In some embodiments, the active sensor is an emitter (or transmitter)/receiver and may transmit and receive signals to determine the presence of a person and/or badge. In some embodiments, the that active sensor transmits and receives, for example, an infrared signal to detect the presence of a person or asset (whether or not the person has a badge 104 or not). Other types of active detectors that continuously (or periodically) search for a badge or person may be included. In some embodiments, multiple transmitters and/or receivers are employed by the people counter 107, such as, for example, multiple infrared emitters/receivers. In such an embodiment, people counter 107 may be used to determine the direction of travel for a person 105. Exemplary embodiments of people counters are disclosed infra.

In some embodiments, people counter 107 has an indicator (not shown), such as a light or speaker and indicates that it has detected a badge 104 within range. In some embodiments, the indicator indicates the presence of one or more persons irrespective of whether a badge is associated with the one or more persons.

People counter 107 (and the people counters disclosed infra) may transmit signals indicative of one or more of the following to the gateway 106 and/or compliance monitoring station 108: a signal indicative of a people counter identifier (such as a serial number); a signal indicative of location identifier; a signal indicative of a strength of signal; a signal indicative of strength of signal received from a badge; a signal indicative of a badge identifier (such as a serial number); a signal indicative of the presence of a person, a signal indicative of the presence of a badge or an asset; a signal indicative of the time of detection of a badge, person, or asset; a signal indicative of detecting a badge and person or asset.

In some embodiments, dispenser 102 transmits signals 111 to compliance monitoring station 108, which may be through gateway 106 and or one or more repeaters (not shown). In some embodiments, dispenser 102 receives signals 111 from compliance monitoring station 108. In some embodiments, signals 111 are one-way signals from the dispenser 102 to the compliance monitoring station 108. In some embodiments, the signals are indicative of at least one of a dispenser function, a dispenser identification, a badge identification, a dispenser parameter, signals similar to those described above with respect to the people counter 107 and the like.

In some embodiments, badge 104 transmits signals 112 to compliance monitoring station 108. In some embodiments, badge 104 receives signals 112 from compliance monitoring station 108. In some embodiments, the signals are indicative of at least one of a dispenser function, a dispenser identification, a badge identification, a dispenser parameter, and the like. In some embodiment, the signals 112 are routed through one or more repeaters 106. The dispenser functions may be indicative of, for example, a dispense event, a refill level, a dispenser error, an incorrect or unauthorized refill, a dispenser malfunction, or the like.

Figure 2:
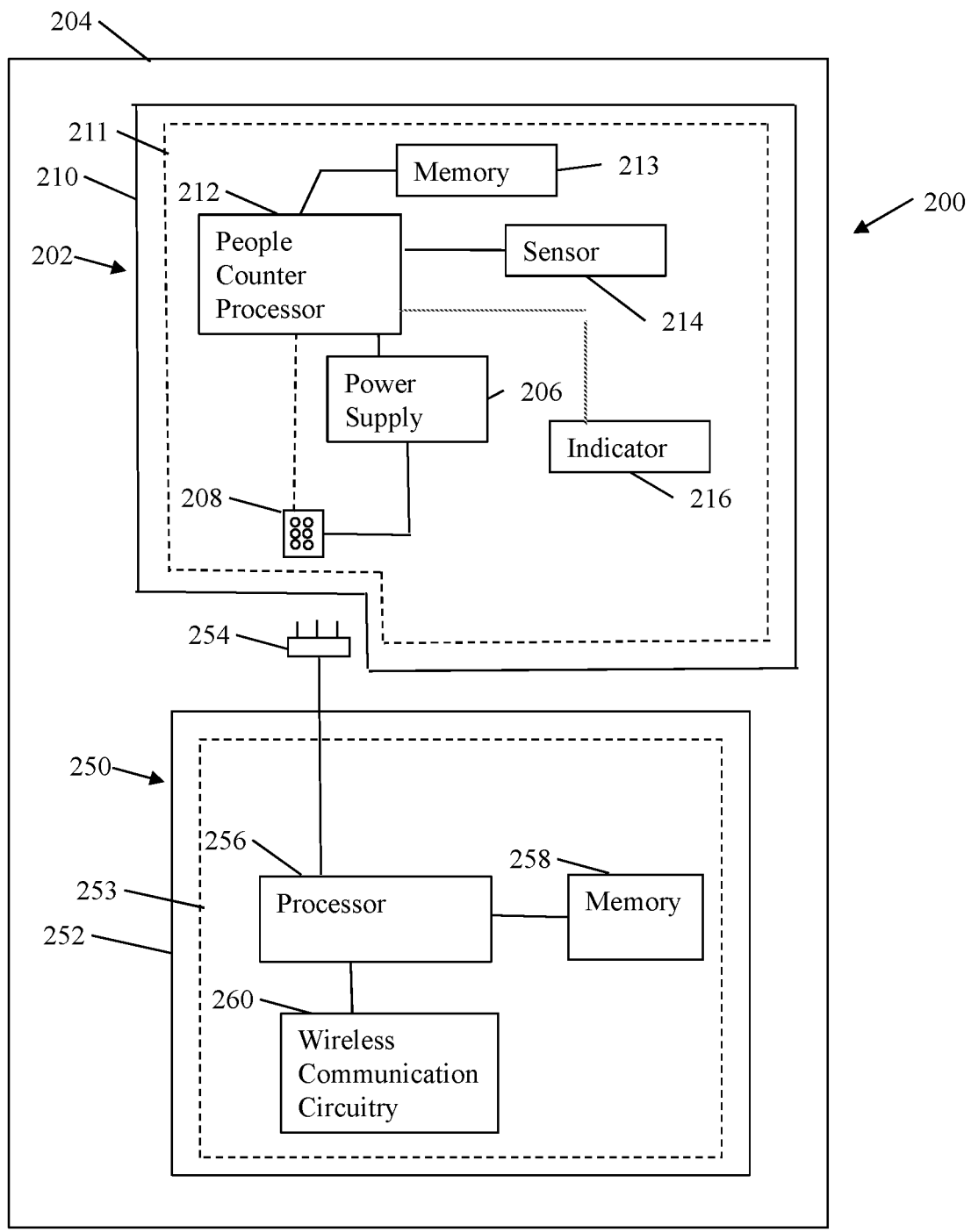
FIG. 2 is a schematic block diagram of an exemplary embodiment of a modular people counter.

FIG. 2 is an exemplary embodiment of a modular people counter 200 that may be use with compliance monitoring systems. Modular people counter 200 includes a people counter base 202 and a communications module 250. Unless expressly stated otherwise, the term "people counter" as used herein is broader than counting people. For example, a people counter can be used to determine whether a person is present, whether a badge is present and/or whether an asset is present in the monitored area.

In some embodiments, people counter base 202 has a people counter base housing 210 and communications module 250 has a communications module housing 252. In some embodiments, there is not a base housing 210 or communications housing 252, but rather the people counter base circuitry 211 is located on one or more circuit boards and communications module 250 circuitry 253 is located on one or more separate circuit boards in optional housing 204. In some embodiments, people counter base 210 include base housing 210 and communications module 253 includes communications module 253 and are also enclosed by optional housing 204.

People counter base 202 includes a people counter processor 212. People counter processor 212 may be any type of processor, such as, for example, a microprocessor or microcontroller, discrete logic, such as an application specific integrated circuit (ASIC), other programmed logic device or the like. Processor 212 is in circuit communications with a connector 208.

Connector 208 may be a communication port or standard plug in type connector. In some embodiments, connector 208 is a communication port is a plug type connector that allows a user to connect to the people counter circuitry 211 to: program, re-program or update the software or logic, run diagnostics on the people counter circuitry 211 and/or retrieve information from the people counter circuitry 211 depending on the people counter configuration.

People counter processor 212 is in circuit communication with memory 213. Memory 213 may be any type of memory, such as, for example, Random Access Memory (RAM); Read Only Memory (ROM); programmable read-only memory (PROM), electrically programmable read-only memory (EPROM), electrically erasable programmable read-only memory (EEPROM), flash, magnetic disk or tape, optically readable mediums including CD-ROM and DVD-ROM, or the like, or combinations of different types of memory. In some embodiments, the memory 213 is separate from the processor 212, and in some embodiments, the memory 213 resides on or within processor 212.

A power source 206, such as, for example, one or more batteries, is also provided. The power source 206 is preferably designed so that the power source 206 does not need to be replaced for the life of the people counter 202. Power source 206 is in circuitry communication with people counter processor 212 sensor 214, connector 208, and optional indicator 216. The power source 206 is in circuit communication with voltage regulator circuitry (not shown). In one exemplary embodiment, voltage regulator circuitry (not shown) provides regulated power to processor 212, sensor 214, and connector 208.

Processor 212 is in circuit communication with a sensor 214 for detecting whether or not a person or a badge is present in the monitored area. In some embodiments, sensor 214 may be any type of passive or active sensor, such as, for example, an infrared sensor and detector, a proximity sensor, an imaging sensor, a thermal sensor; wireless signal receiving circuitry, an RFID detector; and RF sensor/detector, or the like.

In addition, processor 212 is in circuit communication with optional indicator 216. Optional indicator 216 may be any type of indicator, such as, for example, a visual indicator or audible indicator. In some embodiments, a visual indicator is a light. In some embodiments, an audible indicator includes a speaker.

Communications module 250 is configured to communicate with compliance provider's proprietary components. Accordingly, communications module 250 may include the below described components, and/or may include other components (not shown) that are necessary to communicate with the selected compliance provider's proprietary components. Accordingly, multiple communications modules 250 would typically be stocked to accommodate multiple compliance providers.

Exemplary communications module 250 includes a module processor 256. Module processor 256 may be any type of processor, such as, for example, a microprocessor or microcontroller, discrete logic, such as an application specific integrated circuit (ASIC), other programmed logic device or the like. Module processor 256 is in circuit communications with a mating connector 254, memory 258 and wireless communication circuitry 260. In some embodiments module processors are not used and the base processor is configured to operate the wireless communication circuitry in the modules.

Communications module memory 258. Memory 258 may be any type of memory, such as, for example, Random Access Memory (RAM); Read Only Memory (ROM); programmable read-only memory (PROM), electrically programmable read-only memory (EPROM), electrically erasable programmable read-only memory (EEPROM), flash, magnetic disk or tape, optically readable mediums including CD-ROM and DVD-ROM, or the like, or combinations of different types of memory. In some embodiments, the memory 258 is separate from the processor 256, and in some embodiments, the memory 258 resides on or within processor 256.

Mating connector 254 mates with connector 208. Typically mating connector 254 mates with connector 208 with a "plug" type connector. In some embodiments, mating connector 208 provides power to communications module 250 and wireless communication circuitry 260. In some embodiments, a separate power source (not shown), such as, for example, one or more batteries, provides power to the communication device. In addition, people counter processor 212 may provide any of the signals described above with respect to compliance system shown and described with respect to FIG. 1 that may be communicated to or by a badge, a dispenser, a gateway, a repeater, or a compliance monitoring station.

Communications module 250 wirelessly transmits the signals through wireless communication circuitry 260.

In some embodiments, wireless communication circuitry 260 includes long range wireless communication circuitry. In a first such embodiment, wireless communication circuitry 260 includes Wifi circuitry. In a second such embodiment, wireless communication circuitry 260 includes Lora circuitry. In a third such embodiment, wireless communication circuitry 260 includes Zigbee circuitry. In a fourth such embodiment, wireless communication circuitry 260 includes Wifi circuitry. In a fifth such embodiment, wireless communication circuitry 260 includes 900 Mhz circuitry. In a sixth such embodiment, wireless communication circuitry 260 includes MiWi circuitry, and in a seventh such embodiment, wireless communication circuitry 260 includes cellular circuitry.

In some embodiments, wireless communication circuitry 260 includes near field wireless communication circuitry. In a first such embodiment, wireless communication circuitry 260 includes BLE circuitry. In a second such embodiment, wireless communication circuitry 260 includes ANT circuitry. In a third such embodiment, wireless communication circuitry 260 includes IR circuitry. In a fourth such embodiment, wireless communication circuitry 260 includes NFC circuitry.

In some embodiments, wireless communication circuitry 260 includes both long range wireless communication circuitry and near field communications circuitry. In a first such embodiment, wireless communication circuitry 260 includes one or more of the above long range wireless communication circuitries and one or more of the above near field communication circuitries.

Figure 3:
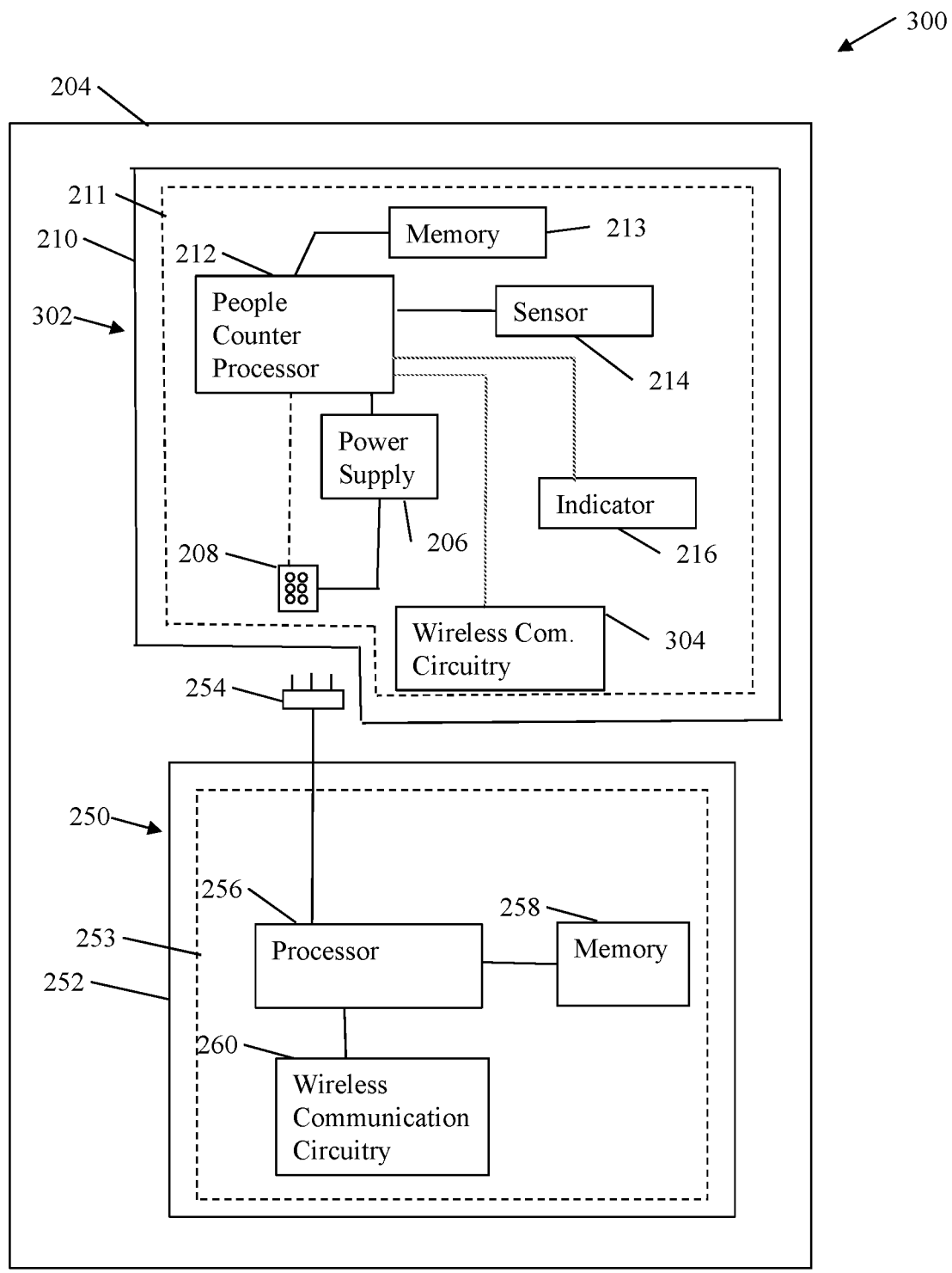
FIG. 3 is a schematic block diagram of another exemplary embodiment of a modular people counter.

FIG. 3 is another schematic block diagram of an exemplary modular people counter 300. Modular people counter 300 is similar to module people counter 200 and like numbered components are not re-described herein. In this exemplary embodiment, people counter base 302 includes near field wireless communication circuitry 304. In some embodiments, the near field wireless communication circuitry 304. In a first such embodiment, wireless communication circuitry 304 includes BLE circuitry. In a second such embodiment, wireless communication circuitry 304 includes ANT circuitry. In a third such embodiment, wireless communication circuitry 304 includes IR circuitry. In a fourth such embodiment, wireless communication circuitry 304 includes NFC circuitry.

Figure 4:
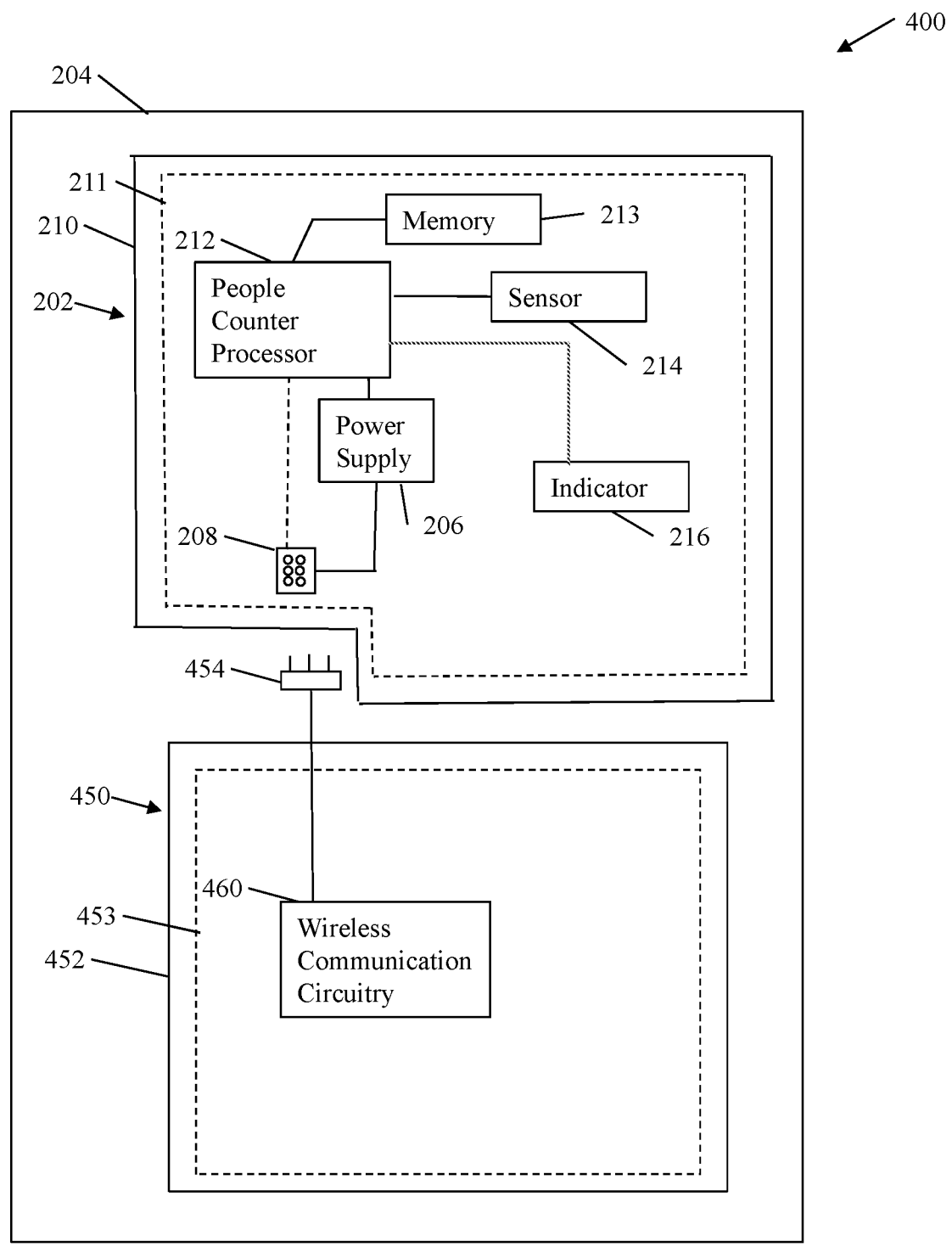
FIG. 4 is a schematic block diagram of another exemplary embodiment of a modular people counter.

FIG. 4 is another schematic block diagram of a modular people counter 400. The base 202 of modular people counter 400 is similar to module people counter 200 and like numbered components are not re-described herein. As described above with respect to the housings, communications module 450 includes a module housing 452. In some embodiments, there is not a housing 452, but rather communications module 450 circuitry 453 is located on one or more separate circuit boards. In some embodiments, people counter base 210 and communications module 253 are enclosed by optional housing 204.

Mating connector 454 mates with connector 208. Mating connector 454 provides power to wireless communication circuitry 460 and provides a signal path between people counter processor 212 and wireless communication circuitry 460. In some embodiments a separate power source is used to power wireless communication circuitry 460. People counter processor 212 may provide any of the signals described above with respect to compliance system shown and described with respect to FIG. 1 that may be communicated to a badge, a dispenser, a gateway, a repeater, or a compliance monitoring station.

Communications module 240 wirelessly transmits the signals through wireless communication circuitry 460. In some embodiments, wireless communication circuitry 460 includes long range wireless communication circuitry. In a first such embodiment, wireless communication circuitry 460 includes Wifi circuitry. In a second such embodiment, wireless communication circuitry 460 includes Lora circuitry. In a third such embodiment, wireless communication circuitry 460 includes Zigbee circuitry. In a fourth such embodiment, wireless communication circuitry 460 includes Wifi circuitry. In a fifth such embodiment, wireless communication circuitry 460 includes 900 Mhz circuitry. In a sixth such embodiment, wireless communication circuitry 460 includes MiWi circuitry, and in a seventh such embodiment, wireless communication circuitry 460 includes cellular circuitry.

In some embodiments, wireless communication circuitry 460 includes near field wireless communication circuitry. In a first such embodiment, wireless communication circuitry 460 includes BLE circuitry. In a second such embodiment, wireless communication circuitry 460 includes ANT circuitry. In a third such embodiment, wireless communication circuitry 460 includes IR circuitry. In a fourth such embodiment, wireless communication circuitry 460 includes NFC circuitry.

Figure 5:
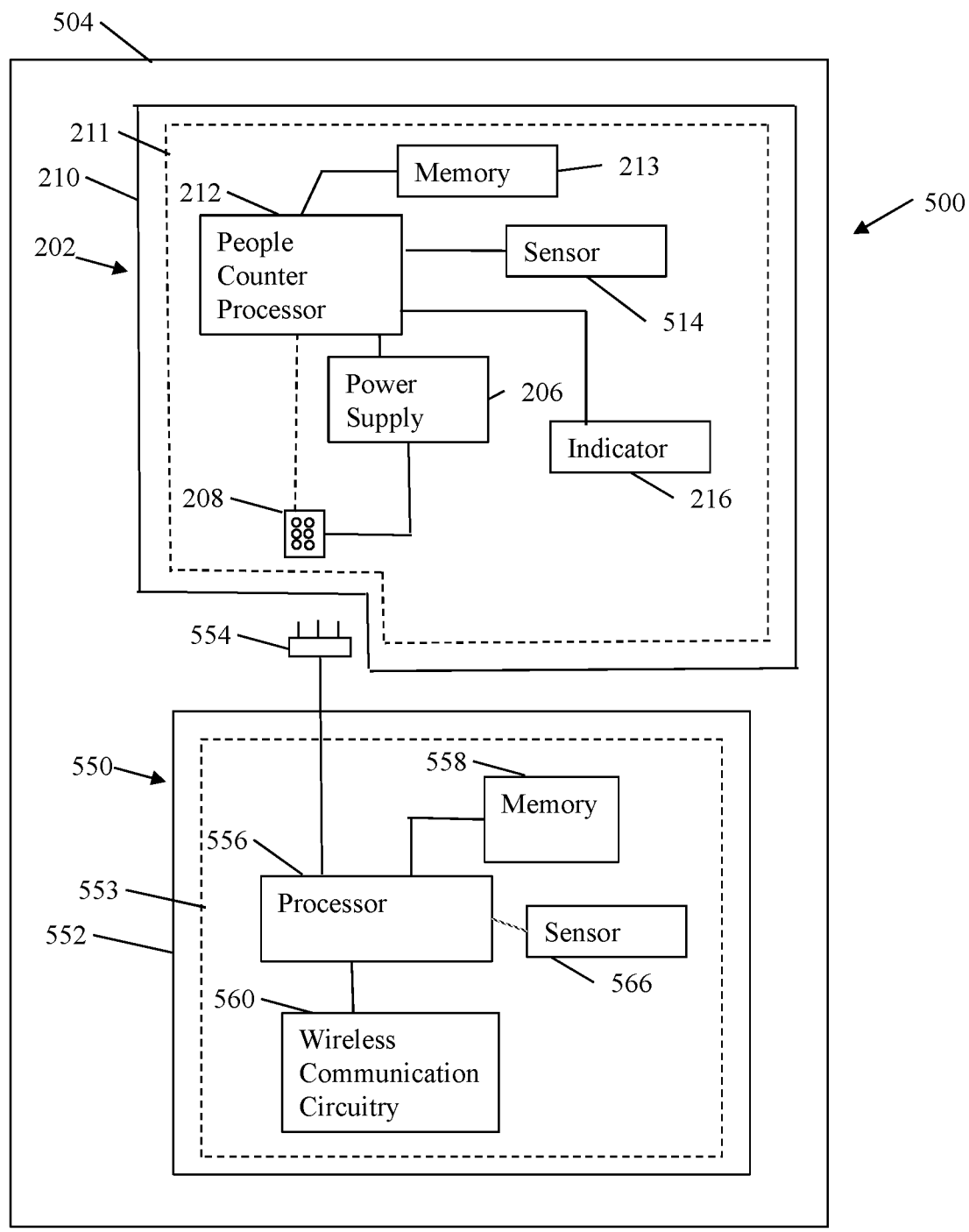
FIG. 5 is another schematic block diagram of an exemplary embodiment of a modular people counter.

FIG. 5 illustrates another exemplary an exemplary embodiment of a modular people counter 500 for use with compliance monitoring systems. People counter base 202 is similar to people counter base 202 described above and is not re-described herein.

In this exemplary embodiment, processor 212 is in circuit communication with a sensor 514 for detecting the presents of one or more persons in the monitored area. Sensor 514 may be any type of passive or active sensor, such as, for example, a passive infrared sensor, an active infrared sensor, a proximity sensor, an imaging sensor, a thermal sensor, and RF sensor or the like that may be used to detect one or more persons.

Mating connector 554 mates with connector 208 to provide power to communications module 550, wireless communication circuitry 560 and sensor 566. In some embodiments a separate power supply provides power for communications module 550. In addition, people counter processor 212 may provide any of the signals described above with respect to compliance system shown and described with respect to FIG. 1 that may be communicated to a badge, a dispenser, a gateway, a repeater, or a compliance monitoring station.

In addition, communications module 550 includes a sensor 566. Sensor 566 is used to detect one or more badges (not shown). The badges may be associated with one or more people (detected by sensor 514) or associated with one or more assets. Sensor 566 may include circuitry used to detect signals emitted from badges, such as, for example, BLE signals, BlueTooth signals, ANT signals, RF signals, IR signals and the like.

In some embodiments, people counter processor 212 provides a "wake up" signal for communications module 550 and or sensor 566 to wake up and scan for a signal from a badge or other transmitting device upon detection of a person or badge by sensor 514. Use of the "wake up" signal conserves power supply 206 (or a separate power supply (not shown) for module 550). Accordingly, communications module 550 and sensor 566 need only be active and scanning for a badge after sensor 514 has already determined that a person or badge is within the selected area.

Accordingly, people counter 500 can send signals indicative of the presence of one or more people located within the monitored area, the presence of one or more badges (whether or not those badges are associated with one or more of the people located within the monitored area), badge identification; dispenser identification; dispenses; and the like; and/or other signals that have been described more fully herein.

Communications module 550 wirelessly transmits the signals through wireless communication circuitry 560.

In some embodiments, wireless communication circuitry 560 includes long range wireless communication circuitry. In a first such embodiment, wireless communication circuitry 560 includes Wifi circuitry. In a second such embodiment, wireless communication circuitry 560 includes Lora circuitry. In a third such embodiment, wireless communication circuitry 560 includes Zigbee circuitry. In a fourth such embodiment, wireless communication circuitry 560 includes Wifi circuitry. In a fifth such embodiment, wireless communication circuitry 560 includes 900 Mhz circuitry. In a sixth such embodiment, wireless communication circuitry 560 includes MiWi circuitry, and in a seventh such embodiment, wireless communication circuitry 560 includes cellular circuitry.

In some embodiments, wireless communication circuitry 560 includes near field wireless communication circuitry. In a first such embodiment, wireless communication circuitry 560 includes BLE circuitry. In a second such embodiment, wireless communication circuitry 560 includes ANT circuitry. In a third such embodiment, wireless communication circuitry 560 includes IR circuitry. In a fourth such embodiment, wireless communication circuitry 560 includes NFC circuitry.

In some embodiments, wireless communication circuitry 560 includes both long range wireless communication circuitry and near field communications circuitry. In a first such embodiment, wireless communication circuitry 560 includes one or more of the above long range wireless communication circuitries and one or more of the above near field communication circuitries.

Figure 6:
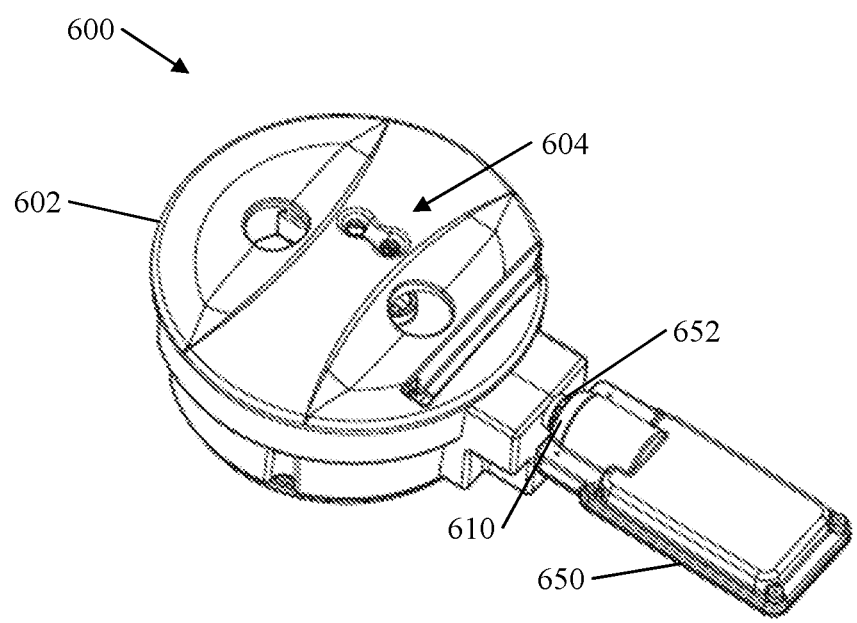
FIG. 6 is a prospective view of an exemplary modular people counter.

FIG. 6 is a prospective view of an exemplary embodiment of a modular people counter 600. Modular people counter 600 includes a base 602. Base 602 includes one or more sensors 604 and may include the components and circuitry identified above. Base 602 includes a housing 606 and a connector 610. Connector 610 is in circuit communication with the base circuitry located inside base 602. A communications module 650 is attached to people counter base 602 via connector 610 and mating connector 652. Communications module 650 may include the components and circuitry described above with respect to the other communications modules. The circuitry is in circuit communications with mating connector 652 and is this in circuit communications with the base circuitry. A plurality of different communications modules 650 may be stocked to work with different compliance monitoring providers and may be plugged into people counter base 602. Thus, people counter base 602 may be used for many different proprietary compliance monitoring providers' equipment. In addition, should a communications module fail, the communications module may be replaced without having to replace the people counter base 602.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. It is not the intention of the applicant to restrict or in any way limit the scope of the appended claims to such detail. Unless expressly excluded herein, all such combinations and sub-combinations are intended to be within the scope of the present inventions. Still further, while various alternative embodiments as to the various aspects, concepts and features of the inventions—such as alternative materials, structures, configurations, methods, circuits, devices and components, software, hardware, control logic, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order in which the steps are presented to be construed as required or necessary unless expressly so stated.

We claim:
1. A modular people counter comprising:
   a base;
      the base having:
      a people counter processor;
      a memory;
      a power supply having one or more batteries;
      a passive sensor that detects whether a badge and/or a person has entered into a selected area and is within a sensing range;
      a first mating connector;
      wherein the first mating connector is in circuit communication with the people counter processor; and
   a communications module;
      the communications module having a second mating connector for connecting to the first connector and a wireless communications circuitry;
   wherein the communications module is configured to receive one or more signals from the people counter processor when the first mating connector and the second mating connector plug into one another; and
   wherein the people counter processor is in close proximity of the wireless communications circuitry when the first mating connector and the second mating connector are connected together; and wherein the communications module includes an active sensor and the active sensor is activated upon detection of the badge by the passive sensor.

2. The modular people counter of claim 1 wherein the communications module comprises a wireless communications module processor.

3. The modular people counter of claim 1 wherein the first mating connector is in circuit communications with the power supply and wherein the second mating connector connects to the first mating connector to provide power to the communications module.

4. The modular people counter of claim 1 wherein the people counter base is configured to determine a direction of travel of the badge and/or person.

5. The modular people counter of claim 1 wherein the wireless communications circuitry includes long range communications circuitry.

6. The modular people counter of claim 5 wherein the wireless communications circuitry includes near field communications circuitry.

7. The modular people counter of claim 1 wherein the wireless communications circuitry includes long range communications circuitry and near field communications circuitry.

8. The modular people counter of claim 1 wherein the people counter base further comprises visual or audible indicator that indicates detection of the badge.

9. The modular people counter of claim 1 wherein the base is located at least partially in a first housing and the communication module is located at least partially in a second housing.

10. A modular people counter comprising:
a base;
the base having:
a base housing;
an opening in the base housing;
a people counter processor;
a memory; a power source;
a people sensor that detects whether one or more people or badges have entered into a monitored area and are within the people sensor's sensing range; and
a first connector;
the first connector located proximate to the opening in the base housing;
the first connector in circuit communication with the people counter processor; and
a first communications module;
a first communications module housing;
a first wireless communications circuitry;
wherein the first wireless communications circuitry is configured to receive one or more signals from the people counter processor;
the first communications module configured to communicate with a first proprietary compliance monitoring provider's equipment;
the first communications module having a first communications module connector for connecting to the first connector;
wherein the first communications module connector is located at least partially in the first communications module housing;
a second communications module;
a second communications module housing;
a second wireless communications circuitry;
wherein the second wireless communications circuitry is configured to receive one or more signals from the people counter processor;
the second communications module configured to communicate with a second proprietary compliance monitoring provider's equipment;
the second communications module having a second communications module connector for connecting to the first connector;
wherein the second communications module connector is located at least partially in the second communications module housing;
wherein if the modular people counter is being used with the first compliance monitoring provider's equipment, the first communications module connector is connected to the first connector; and
wherein if the modular people counter is being used with the second compliance monitoring provider's equipment, the second communications module connector is connected to the first connector.

11. The modular people counter of claim 10 wherein the wireless communications circuitry includes near field communications circuitry.

12. The modular people counter of claim 10 wherein the wireless communications circuitry includes near field communications circuitry and long range wireless communications circuitry.

13. The modular people counter of claim 10 wherein each of the first and second communications module comprises a wireless communications module processor.

14. The modular people counter of claim 10 wherein the base and wireless communication circuitry are located in separate housings.

15. A modular people counter comprising:
a base;
the base having:
a housing;
a people counter processor;
a memory;
a power source;
an active sensor that detects when a badge and/or person enters a monitored area and when the badge and/or person exits a monitored area; and
a first connector;
the first connector in circuit communication with the people counter processor; and
a plurality of plug-in communications modules;
each of the communications module having
a housing;
a wireless communications circuitry; and
a second connector for connecting to the first connector to place the wireless communications circuitry in circuit communications with the people counter processor;
wherein any one of the plurality of plug-in communications modules may be connected to the first connector;
wherein at least two of the plurality of plug-in communications modules contain different communications protocols, a first communication protocol for communicating with a first propriety compliance monitoring provider's equipment and a second communications protocol for communicating with a second proprietary compliance monitoring provider's equipment;
wherein when the one of the any one of the plurality of plug in communications module is configured to receive one or more signals from the people counter processor when the first connector is connected to the second connector of the any one of the plurality of plug in communications modules.

16. The modular people counter of claim 15 wherein the wireless communications circuitry includes long range communication circuitry and near field communications circuitry.

17. The modular people counter of claim 15 wherein the wireless communications module comprises a wireless communications module processor.

18. The modular people counter of claim 15 wherein the people counter base further comprises an indicator that indicates detection of the badge.

* * * * *